(12) United States Patent
Berndt

(10) Patent No.: US 6,446,020 B1
(45) Date of Patent: Sep. 3, 2002

(54) METHOD OF CALIBRATING THE SAMPLE HEIGHT IN A SAMPLE ANALYZER

(75) Inventor: Klaus W. Berndt, Timonium, MD (US)

(73) Assignee: Becton, Dickinson and Company, Franklin Lakes, NJ (US)

(*) Notice: Subject to any disclaimer, the term of this patent is extended or adjusted under 35 U.S.C. 154(b) by 0 days.

(21) Appl. No.: 09/845,072

(22) Filed: Apr. 27, 2001

(51) Int. Cl.[7] .............................................. G06M 11/02
(52) U.S. Cl. ...................................................... 702/104
(58) Field of Search ..................... 436/43, 50; 422/100, 422/64; 23/230

(56) References Cited

U.S. PATENT DOCUMENTS

| | | | | |
|---|---|---|---|---|
| 3,874,850 A | * | 4/1975 | Sorensen et al. | 23/230 |
| 5,320,808 A | * | 6/1994 | Holen et al. | 422/64 |
| 5,656,499 A | * | 8/1997 | Chupp et al. | 436/43 |
| 5,837,203 A | * | 11/1998 | Godec et al. | 422/100 |
| 5,976,468 A | * | 11/1999 | Godec et al. | 422/100 |
| 6,127,184 A | * | 10/2000 | Wardlaw | 436/50 |

* cited by examiner

Primary Examiner—John S. Hilten
(74) Attorney, Agent, or Firm—Bruce S. Weintraub

(57) ABSTRACT

The present invention relates to the field of quantitative microspectroscopy, and in particular, to a method for calibrating the height of a sample in a sample analyzer device.

16 Claims, 11 Drawing Sheets

METHOD OF CALIBRATING THE SAMPLE HEIGHT IN A SAMPLE ANALYZER

FIELD OF THE INVENTION

The present invention relates to the field of quantitative microspectroscopy, and in particular to a method for calibrating the height of a sample in a sample analyzer.

BACKGROUND OF THE INVENTION

The determination of such blood parameters as the Hematocrit ("HCT"), the Volume of single Red Blood Cells ("RCV"), the Mean Cell Volume ("MCV") and the Red Cell Distribution Width ("RDW") are of eminent clinical interest. Usually, systems based on electrical impedance measurement (Coulter Counter) or based on light scattering (Flow Cytometer) are employed (see. e.g., J. B. Henry, "Clinical diagnosis and management by laboratory methods", W. B. Saunders Company, Philadelphia, 1996, pp. 548 ff. or D. H. Tycko, M. H. Metz, E. A. Epstein, A. Grinbaum, "Flow-cytometric light scattering measurement of red blood cell volume and hemoglobin concentration", Applied Optics 24 (1985), 1355–1365). Impedance counters are complex and expensive instruments that require very careful adjustment and control of instrument and sample parameters. A major disadvantage of flow cytometers is the fact that the parameters of light scattering depend not only on cell volume, but also on the cell's shape.

In 1983, Gray, Hoffman and Hansen proposed a new optical method for determining the volume of cells in a flow cytometer (M. L. Gray, R. A. Hoffman, W. P. Hansen, "A new method for cell volume measurement based on volume exclusion of a fluorescent dye", Cytometry 3 (1983), 428–432). In this method, the cells are suspended in a fluorescent dye, which is unable to penetrate the cell membrane. The level of fluorescence which is produced when a narrow stream of the cell suspension is excited by a focused laser beam will remain constant until a cell arrives in the illuminated region thereby causing a decrease in fluorescence intensity which is directly proportional to the cell's volume. In a flow cytometer, a single cell is passing through the laser-illuminated spot within approximately 10 µs. Due to this short data acquisition time interval, the electronic detection bandwidth has to be relatively large, which results in a poor signal-to-noise ratio and in a low precision for the volume determination.

The available data acquisition time can be significantly increased by suspending the cells in a stationary sample and applying digital imaging fluorescence microscopy (see P. L. Becker, F. S. Fay, "Cell-volume measurement using the digital imaging fluorescence microscope", Biophysical Journal 49 (1986), A465). In the digital fluorescence microscopy approach, a calibration procedure is required in order to determine the cell volume. Recktenwald and co-workers have introduced a method where the calibration is performed by means of optical transparent and non-fluorescent microspheres that are suspended together with the cells (D. Recktenwald, J. Phi-Wilson, B. Verwer, "Fluorescence quantitation using digital microscopy", Journal Physical Chemistry 97 (1993), 2868–2870). The volume of individual spheres is determined by measuring their projection area under the microscope and transforming this number into a volume, assuming an ideal spherical shape. The decrease in fluorescence intensity as a result of the spheres' volume that is being excluded from emitting fluorescence is used as the required calibration parameter. The advantage of this approach is given by the fact that the calibrating particles are located within the sample itself. In other words, a calibration is performed on the very same sample container, and no extra calibration sample is required.

The use of calibration spheres within a cell suspension is not without problems. First, the introduction of the spheres represents an additional step in the workflow. In systems that are designed for high throughput, this additional step would represent a disadvantage. Secondly, Recktenwald and co-workers observed a tendency of the fluorescent dye molecules to settle down on the sphere's surface, which causes an error. Third, if the optical index of refraction of the spheres does not match well with the liquid's index, then refraction-based artifacts in the measured fluorescence intensity occur at the edges of the spheres. And, finally, the use of microspheres can represent a problem, if e.g. a thin sample thickness in the order of a few micrometers or less is needed.

In order to overcome the problems in the prior art, it has been suggested (U.S. Pat. No. 6,127,184 to Wardlaw) to design a cuvette-like optical sample container for the cell suspension that has different optical pathlengths in different areas. In at least one area, the thickness of the liquid layer of undiluted blood is so thin (2 to 7 microns) that monolayers of isolated Red Blood Cells ("RBCs") are formed. In another region, the liquid layer is thicker (7 to 40 microns), and typical chain-like aggregates of RBCs (referred to as "Roleaux" are forming. The thick area is used to determine the HCT, and the thin area is used to determine the RCV. As in the prior art, the blood plasma is stained with a fluorescent dye that is not penetrating into the RBCs.

In a method and apparatus described in U.S. Pat. No. 6,127,184, the optical cuvette is placed under a microscope, illuminated with excitation light, and reemerging fluorescence is measured by means of an imaging photodetector such as a CCD camera. The RCV is determined using the equation $$RCV = \left[1 - \frac{B_{RBC}}{B_P}\right] * A * d$$

where $B_P$ is the fluorescence intensity emerging from an area of known size, A, within a cell-free plasma region. $B_{RBC}$ is the fluorescence intensity emerging from another area of same size, but comprising a single RBC. In practice, $B_P$ is determined by measuring the fluorescence intensity in a cell-free region near a particular RBC, and by extrapolating to the full size, A. In contrast to the HCT determination, the absolute area, A, and the absolute height of the liquid layer, d, have to be known. One could also say that the absolute volume V=A*d in which the single RBC is embedded, has to be known. The area, A, can be easily determined under the microscope. The determination of the height, d, near the RBC is a more complicated problem and is named "calibration".

U.S. Pat. No. 6,127,184 discloses some methods to "calibrate" the optical cuvette, i.e., to determine the height, d. In one method, a square-shaped capillary of known volume is integrated into the cuvette. By measuring the fluorescence intensity reemerging from this capillary, one could obtain a calibration parameter C=intensity/volume. Since the fluorescence intensity per unit area is assumed to be proportional to the height of the cuvette, the height at any location can then be determined via the reemerging fluorescence intensity. However, in practice, integrating a small part such as a pre-fabricated capillary into a plastic disposable can be difficult and costly.

Other methods disclosed in U.S. Pat. No. 6,127,184 include using a step-like change in the cuvette thickness as a means for calibration, and using a molded calibration standard such as a well of accurately controlled height. However, these methods have some drawbacks in that they require the additional step of precision molding which can be difficult and costly.

Consequently, it has been found that there exists a need for calibrating the height of a sample in a sample analyzer, that would not require molded calibration tools of extreme precision.

SUMMARY OF THE INVENTION

It is an objective of the present invention to provide a method for calibrating the sample height in a sample analyzer, and in particular a calibration method that would be exact, but would not require molded calibration tools of extreme precision within the sample analyzer.

According to the present invention, the above objective is achieved by depositing a sample of biological fluid, and preferably, whole blood into a chamber, such as for example, an optical cuvette, whereby the blood plasma contains a dye and preferably, a fluorescent dye, that does not diffuse into the red blood cells. The sample is illuminated with excitation light so that the plasma emits fluorescence radiation, which is detected by, e.g., a microscope's imaging photodetector. The fluorescent dye is selected so that neither the excitation light nor the emitted fluorescence light are absorbed significantly by the red blood cells.

A height value in the single-cell area is then determined by performing the process steps of (a) measuring fluorescence intensity values in cell-free locations within the single-cell area as a function of the focal plane position, (b) determining the full-width-at-half-maximum ("FWHM") of the fluorescence-intensity-versus-focal-plane-position curve, and (c) calculating the height, d, in the single cell area from the quantity FWHM by taking into account the index of refraction of the blood plasma.

DETAILED DESCRIPTION OF THE INVENTION

According to the method of the present invention, a sample of a biological fluid such as, preferably blood, and more preferably, undiluted blood that contains suspended RBCs is deposited into a chamber, such as, for example, an optical cuvette having a thickness that supports the formation of a monolayer of isolated RBCs. In a preferred embodiment, the cuvette is relatively thin and suitable to be positioned onto the sample stage of a fluorescence microscope. A fluorescent dye is added to, and evenly distributed within the liquid sample. The dye is selected so that it does not leak into the RBCs. In other words, only the blood plasma is stained with a fluorescent dye. The dye should absorb excitation light within a spectral region where the absorption within the RBCs is only weak. Since hemoglobin is the dominant absorber in RBCs, the excitation wavelength should preferably be longer than 600 nm. One good candidate dye is TO-PRO-3 (sold, for example, by Molecular Probes, Inc., Eugene, Oreg.), that can be excited within a wavelength range around to 640 nm. Another possible dye would be TO-PRO-5 (also sold by Molecular Probes, Inc.), which also does not penetrate into the RBCs, and can be excited around 750 nm.

The method for calibrating a sample analyzer, which can be preferably, a disposable sample analyzer, and in a more preferred embodiment, a blood sample analyzer, according to the present invention, can be summarized in the following three steps:

Step 1

Measure fluorescence intensity values in cell-free locations within the single-cell area as a function of the focal plane position.

Step 2

Determine the full-width-at-half-maximum, or FWHM, of the fluorescence-intensity-versus-focal-plane-position curve.

Step 3

Calculate the height, d, in the single cell area from the quantity FWHM by taking into account the index of refraction of the blood plasma.

Steps 1 to 3 according to the present invention will now be discussed in more detail.

Figure 1:
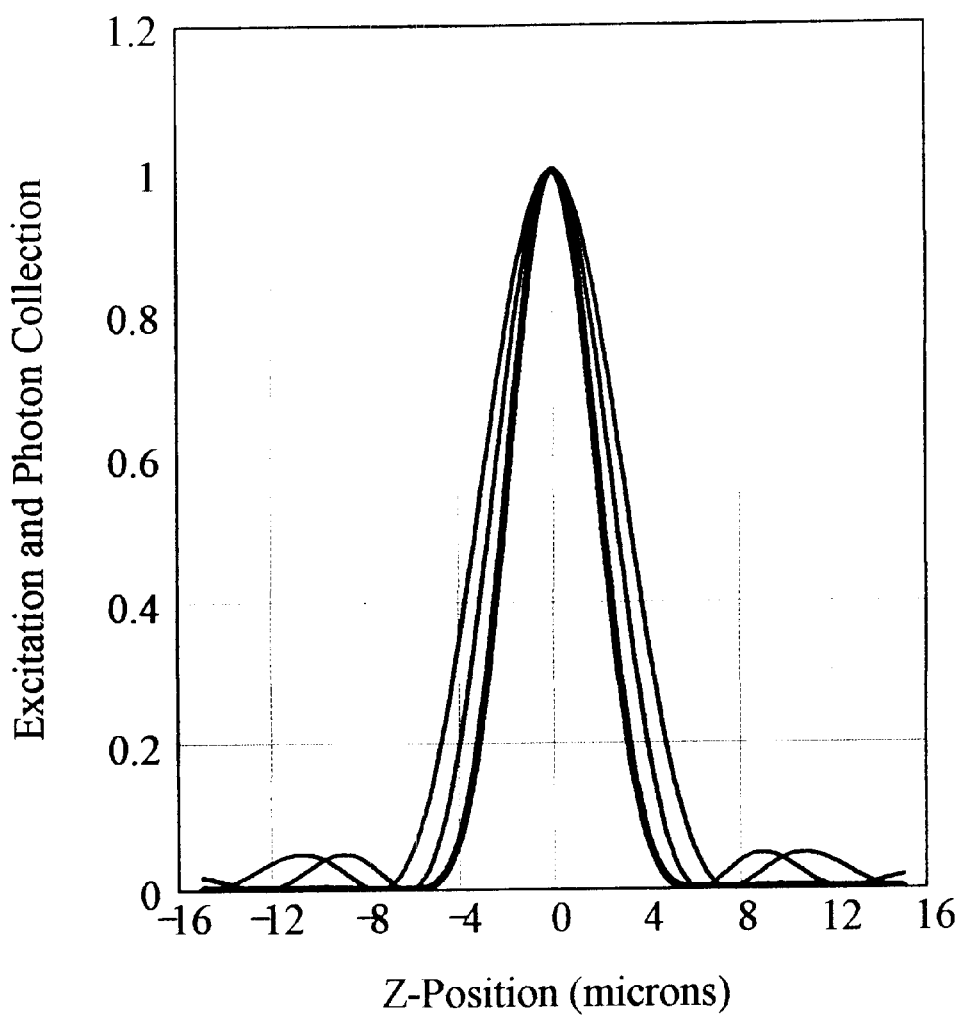
FIG. 1 shows (as the middle bell-shaped profile) the on-axis excitation intensity within the liquid sample as a function of the Z-position for a typical EPI configuration, where the sample is illuminated through the objective lens at an excitation wavelength $\lambda_{ex}$=500 nm, assuming an ideal lens with uniform illumination of the entrance pupil, and a numerical aperture NA=0.4. The cuvette height is 32 microns (−16 . . . +16). The outer bell-shaped curve represents the photon collection efficiency at an emission wavelength $\lambda_{em}$=600 nm. The inner bell-shaped curve represents the combined effect from excitation and photon collection.

FIG. 1 shows (as the middle bell-shaped profile) the on-axis excitation intensity within the liquid sample as a function of the Z-position for a typical EPI configuration, where the sample is illuminated through the objective lens at an excitation wavelength $\lambda_{ex}$=500 nm, assuming an ideal lens with uniform illumination of the entrance pupil, and a numerical aperture NA=0.4. The excitation intensity as a function of Z-position, E(z), can be calculated using the equation $$E(z) = \left[\frac{\sin(u_{ex}(z)/4)}{u_{ex}(z)/4}\right]^2$$

with $$u_{ex}(z) = \frac{2*\pi}{\lambda_{ex}} *(NA)^2 *z$$

where $\lambda_{ex}$ is the excitation center wavelength. The outer bell-shaped curve in FIG. 1 represents the photon collection efficiency, D(z), which can be described by $$D(z) = \left[\frac{\sin(u_{em}(z)/4)}{u_{em}(z)/4}\right]^2$$

with $$u_{em}(z) = \frac{2*\pi}{\lambda_{em}} *(NA)^2 *z$$

wherein $\lambda_{em}$ is the emission center-wavelength. The inner bell-shaped curve in FIG. 1 illustrates the combined effect of E(z) and D(z).

An "EPI configuration" is a common term used in fluorescence microscopy. It means that nearly parallel excitation light is directed towards the objective lens (usually downward). The oncoming excitation light is focused by the objective lens onto the sample, forming a small area of high illumination intensity. Fluorescence light, that is generated within that area of the sample, is collected by the very same objective lens and forms a parallel fluorescence beam going upwards. A parallel beam is formed because the sample should be located almost exactly in the focal plane of the objective lens. Then, there are two overlapping beams above the objective lens (the downward-going excitation beam, and the upward-going fluorescence beam). By inserting, for example, a dichroic beam splitter, one of the beams is split off at an angle of 90°. This is possible because the fluorescence radiation has a longer wavelength than the excitation light. In many microscopes, the excitation beam is split off. In other words, an almost parallel excitation beam reaches a dichroic block, and is directed towards the objective lens. Fluorescence light, generated at the sample, passes straight through the dichroic block and reaches the imaging photodetector, or the observer's eye.

Figure 2:
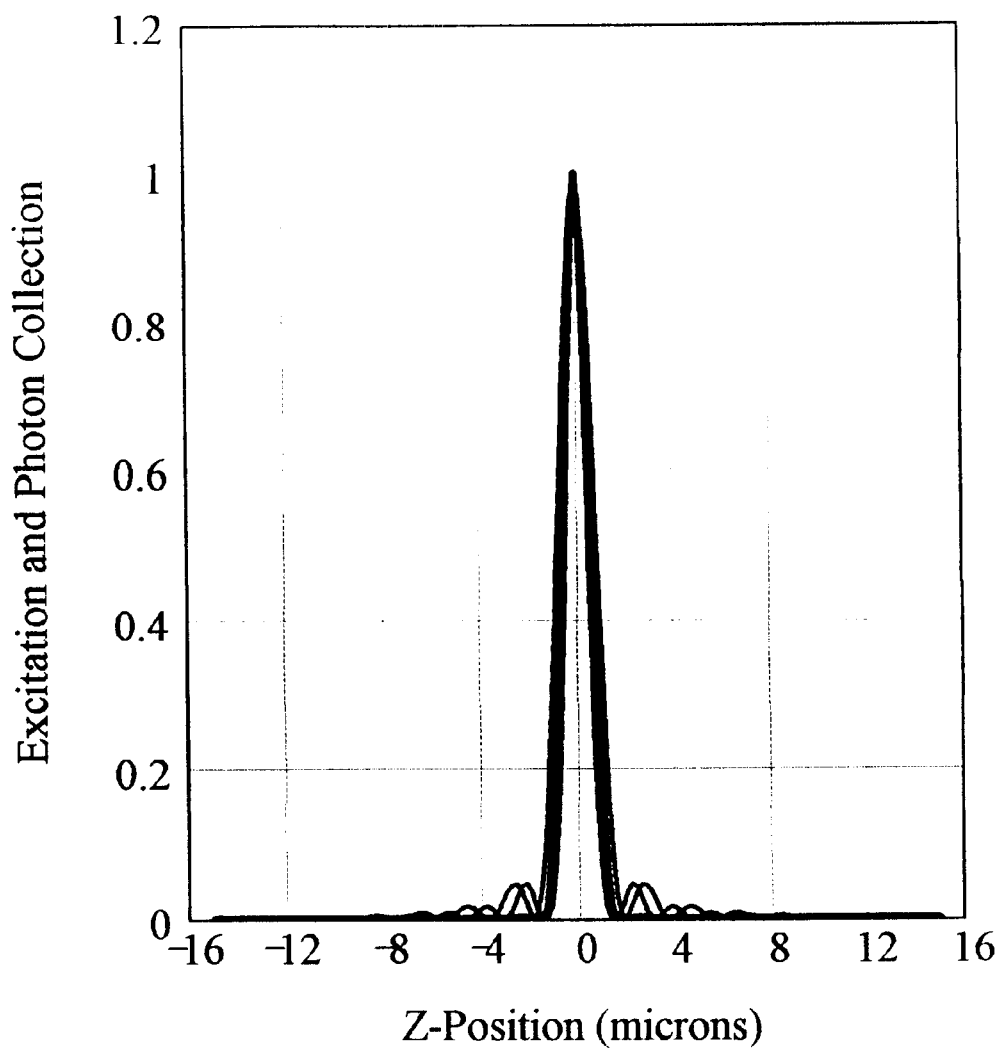
FIG. 2 shows similar plots as in FIG. 1, but for a numerical aperture of 0.8.

As can be seen from FIG. 1, the excitation light is not illuminating the full height of a 32 micron thick cuvette, and the generated fluorescence light is not collected completely either. This effect is even more pronounced for a higher NA value, as illustrated for NA=0.8 in FIG. 2.

The expected fluorescence intensity, $I(z_0)$, as a function of the Z-position of the microscope's focal plane relative to the center of the cuvette, $Z_0$, for a given cuvette height, d, can be calculated using the equation $$I(z_0) = \int_{z_0-d/2}^{z_0+d/2} E(z)*D(z)dz.$$

Figure 3:
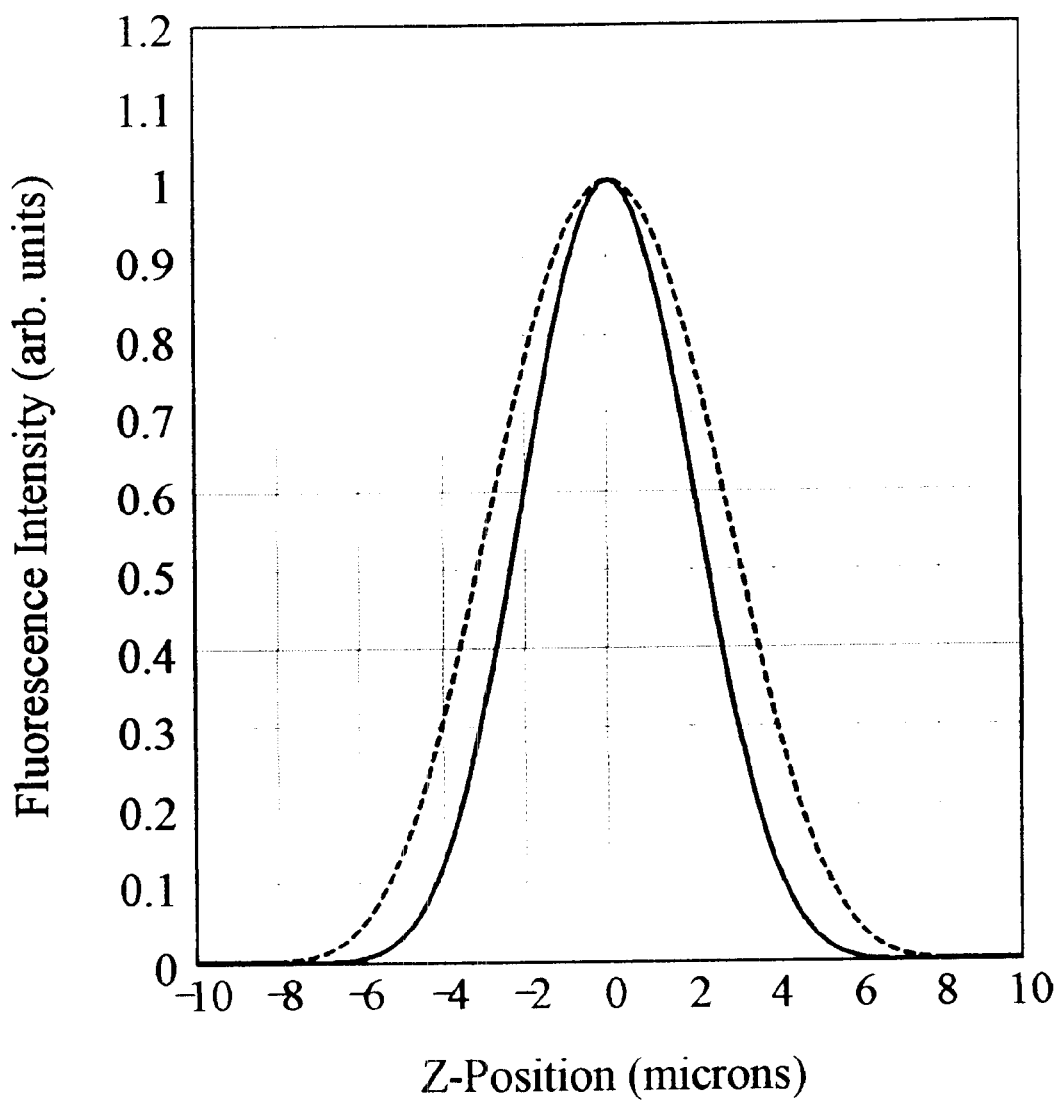
FIG. 3 shows the expected fluorescence intensity as a function of the focal plane position for cuvette heights of 3 microns (solid curve) and 6 microns (dashed curve), assuming a numerical aperture of 0.4.

FIG. 3 illustrates $I(z_0)$ according to this equation for two cuvettes having height values of 3 microns (solid curve) and 6 microns (dashed curve), assuming a numerical aperture of 0.4. In FIG. 3, and in all following figures, we have applied a normalization procedure in that the actual fluorescence intensity is normalized by the maximum fluorescence intensity, which is obtained for $z_0$=0. It has to be emphasized that this normalization is not required for practicing the method according to the present invention, but it improves the illustrative power of the figures.

Figure 4:
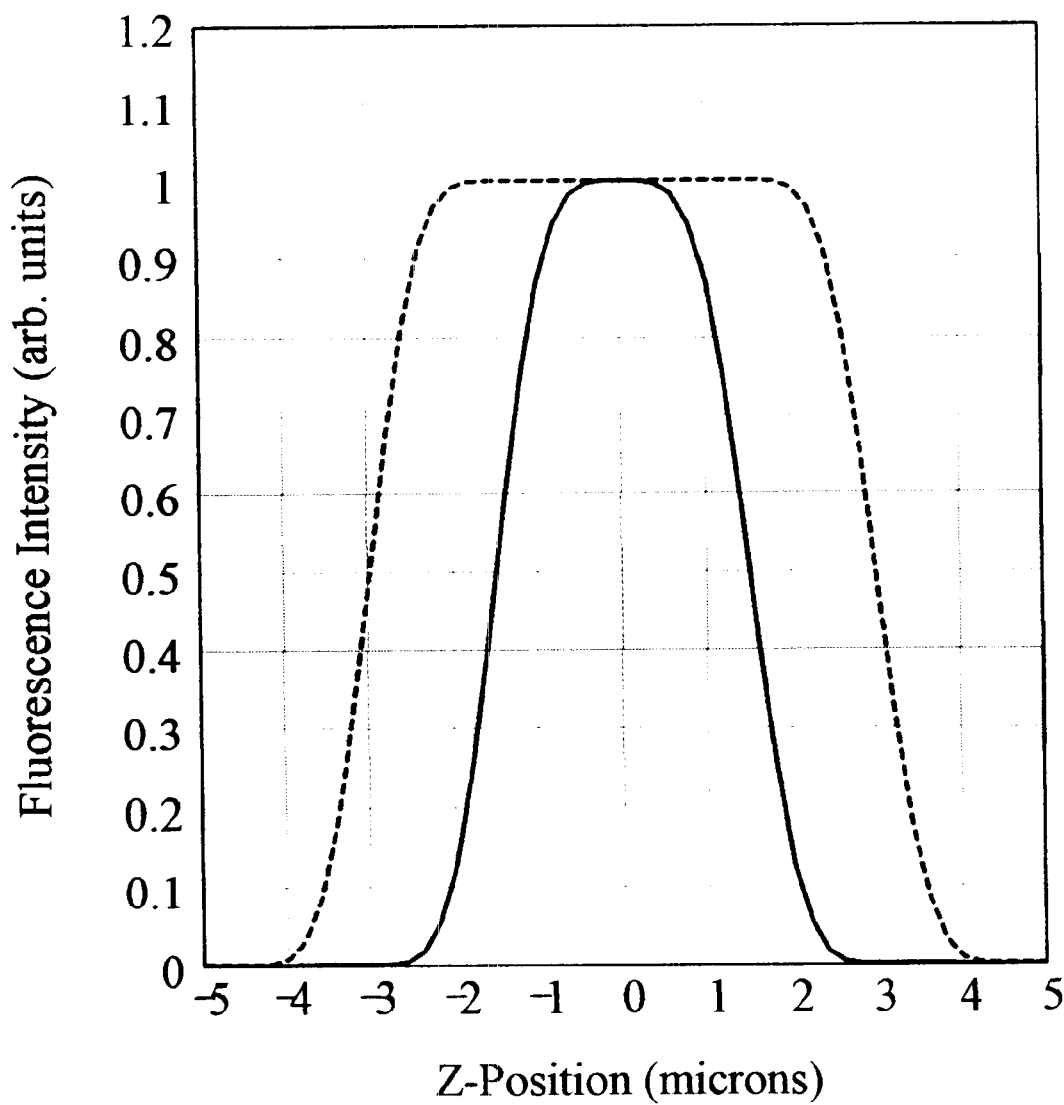
FIG. 4 shows similar plots as in FIG. 3, but for a numerical aperture of 0.8.

From FIG. 3 we see that in the case of NA=0.4 the observed FWHM values are not identical with the true cuvette height. The measured FWHM comes much closer to the true height, if the numerical aperture of the objective lens is increased to NA=0.8 as shown in FIG. 4.

Figure 5:
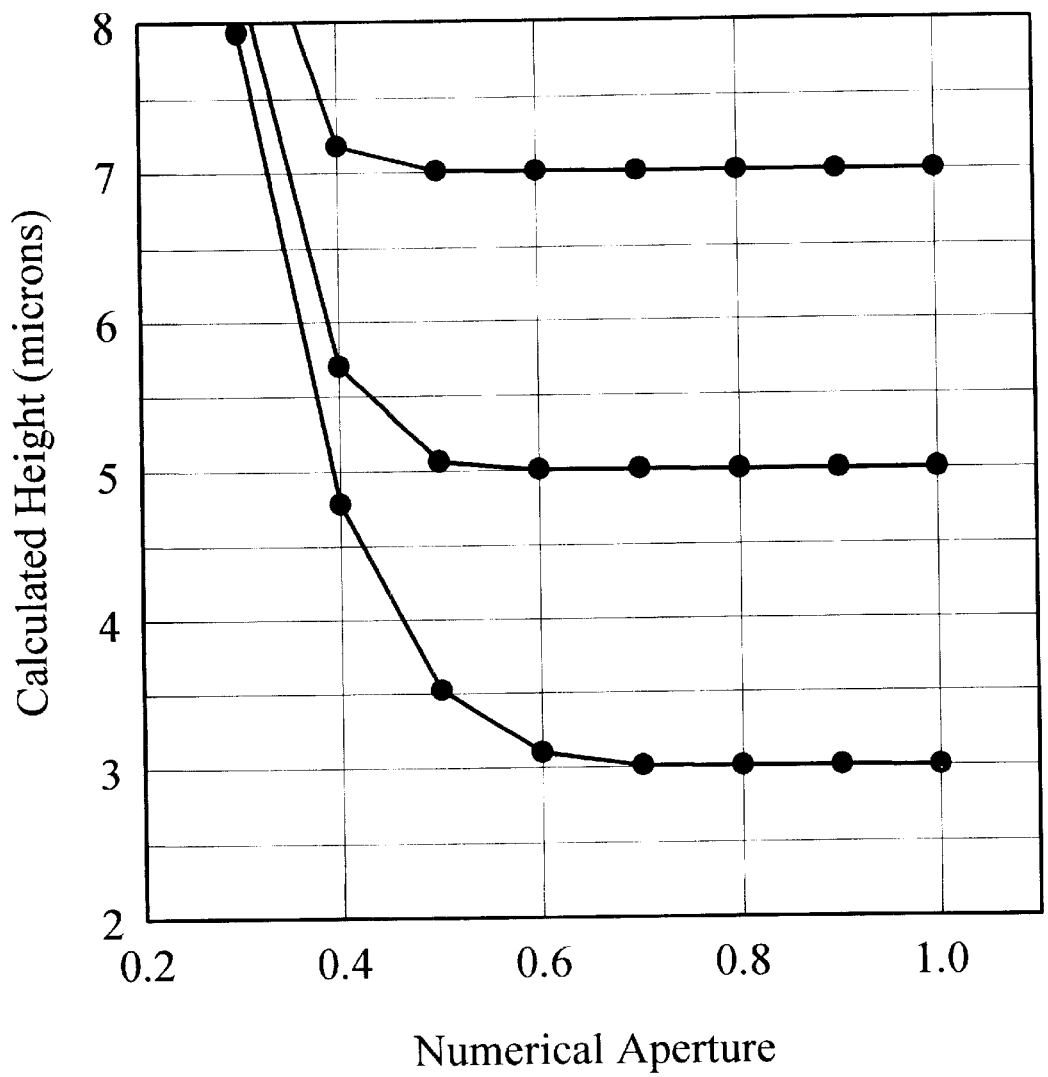
FIG. 5 shows calculated cuvette height values as a function of the numerical aperture that is used, for true height values of 3, 5, and 7 microns.

FIG. 5 shows how much the observed FWHM differs from the true height as a function of the numerical aperture of the objective lens, assuming true height values of 3, 5, and 7 microns, respectively. As can be seen, a numerical aperture NA≧0.7 would be required to determine the height for a disposable having a true height around 3 microns. Lower NA values are required for thicker cuvettes. From FIG. 5 we see that a height around 5 microns can be determined with NA≧0.6, and a height around 7 microns with NA≧0.5. Even lower NA numbers can be applied for still thicker cuvettes.

Figure 6:
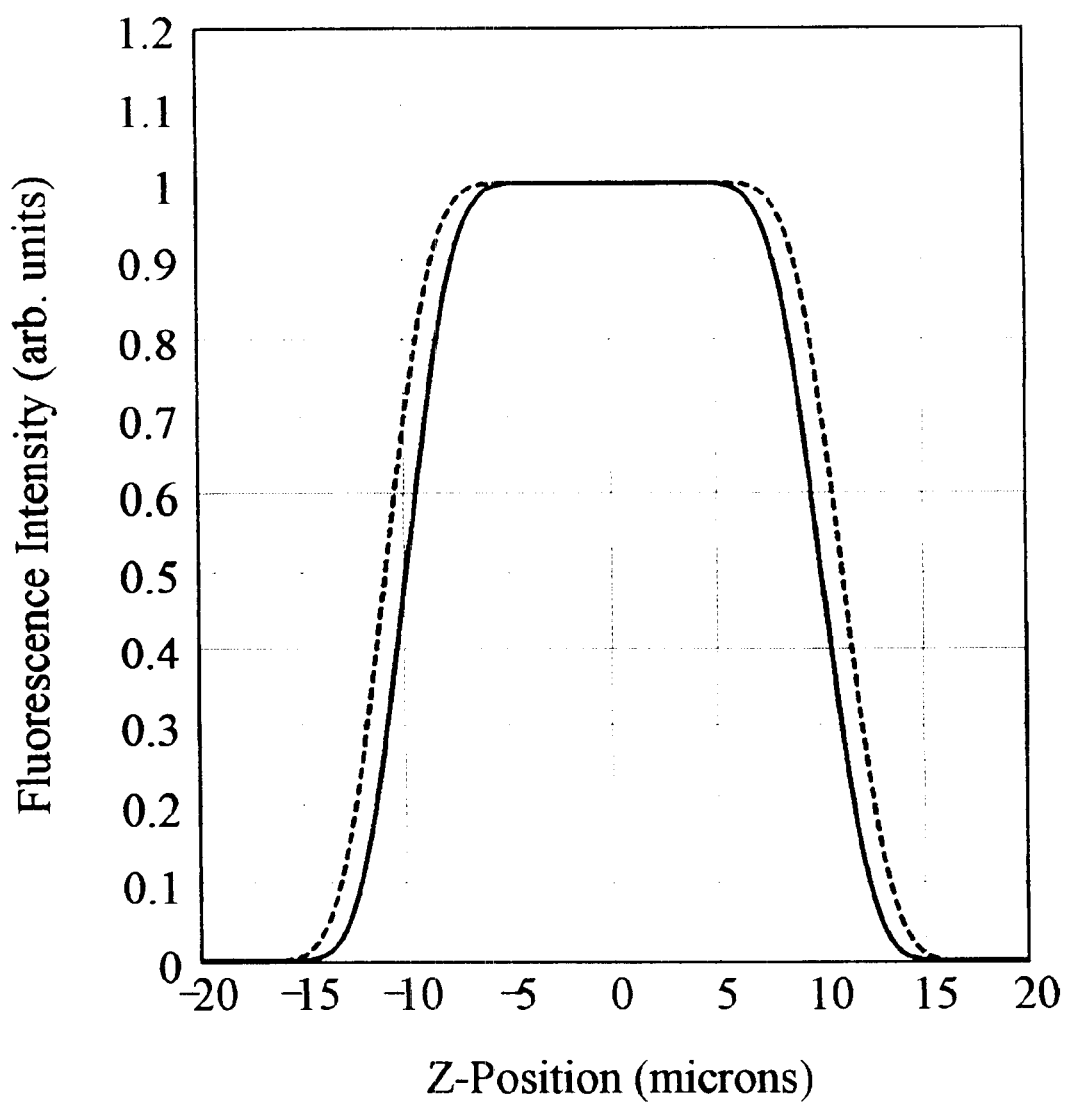
FIG. 6 shows the expected fluorescence intensity as a function of the focal plane position for cuvette heights of 20 microns (solid curve) and 22 microns (dashed curve), assuming a numerical aperture of 0.4.
Figure 7:
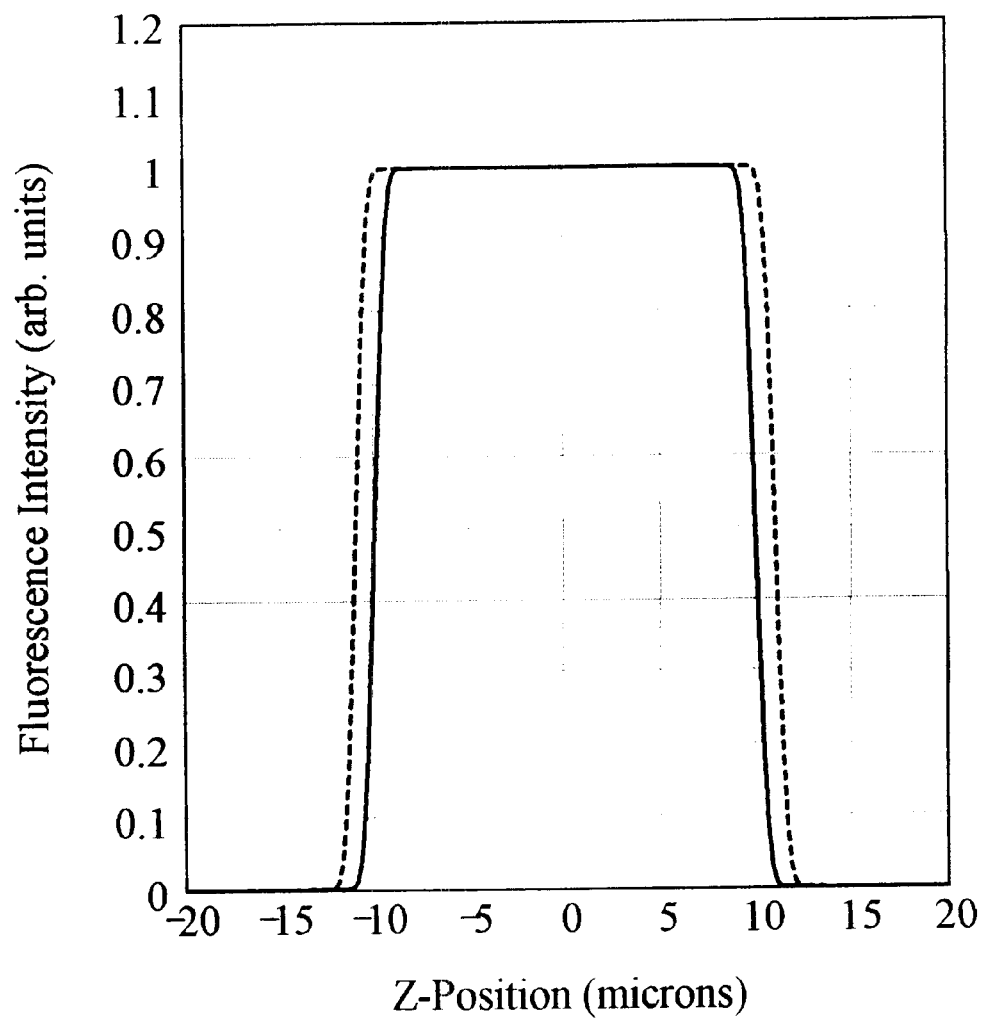
FIG. 7 shows similar plots as in FIG. 6, but for a numerical aperture of 0.8.

The case of thicker cuvettes is illustrated in FIG. 6, where we assume two height values of 20 and 22 microns, respectively, and a numerical aperture NA=0.4. Here we see that the observed FWHM of the fluorescence intensity plot coincides very well with the true height values. An even sharper intensity profile is obtained for NA=0.8, as shown in FIG. 7.

Figure 8:
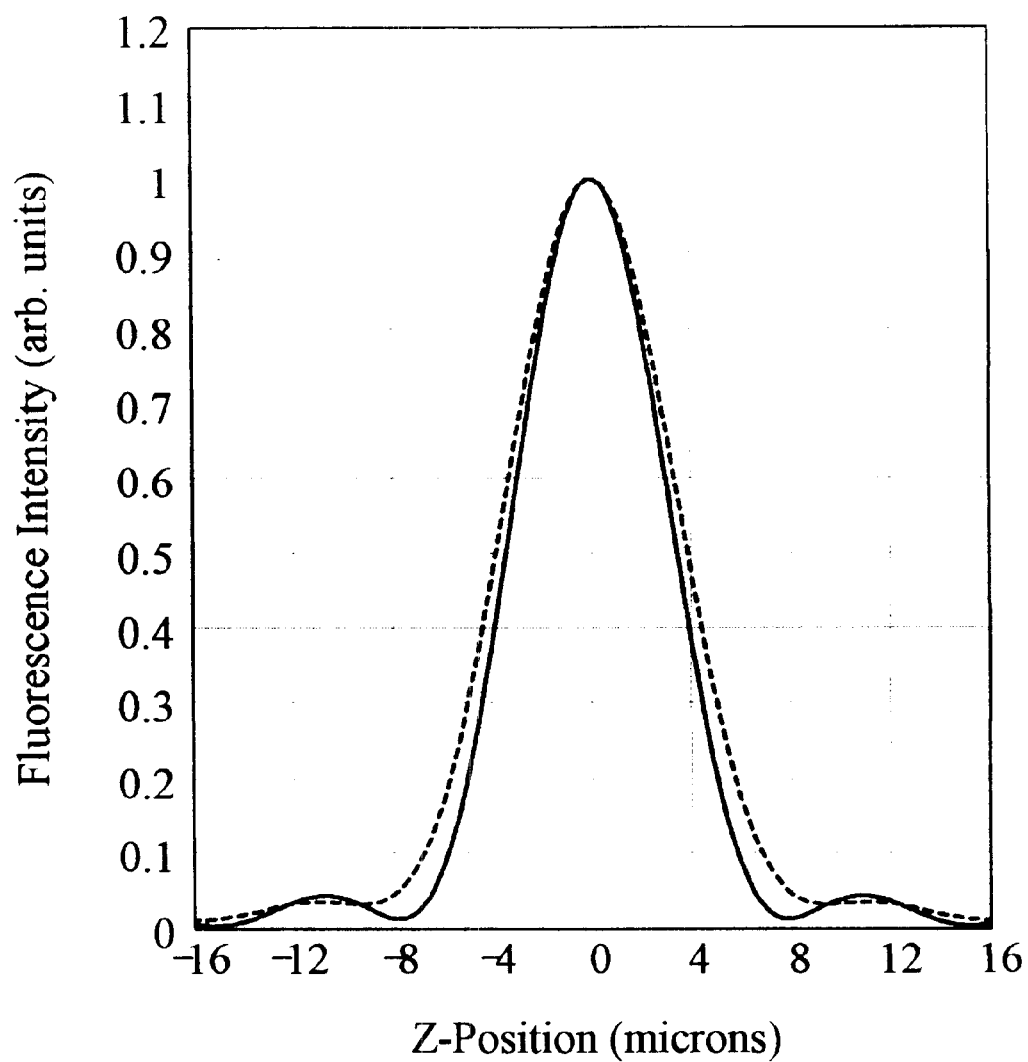
FIG. 8 shows similar plots as in FIG. 3, but assuming that the sample is not illuminated through the objective lens. The numerical aperture is 0.4.

FIG. 8 shows similar plots as in FIG. 3, but assuming that the sample is not illuminated through the objective lens. The numerical aperture is 0.4. As in FIG. 3, the observed FWHM's do not coincide with the true height values, 3 and 6 microns, respectively.

Figure 9:
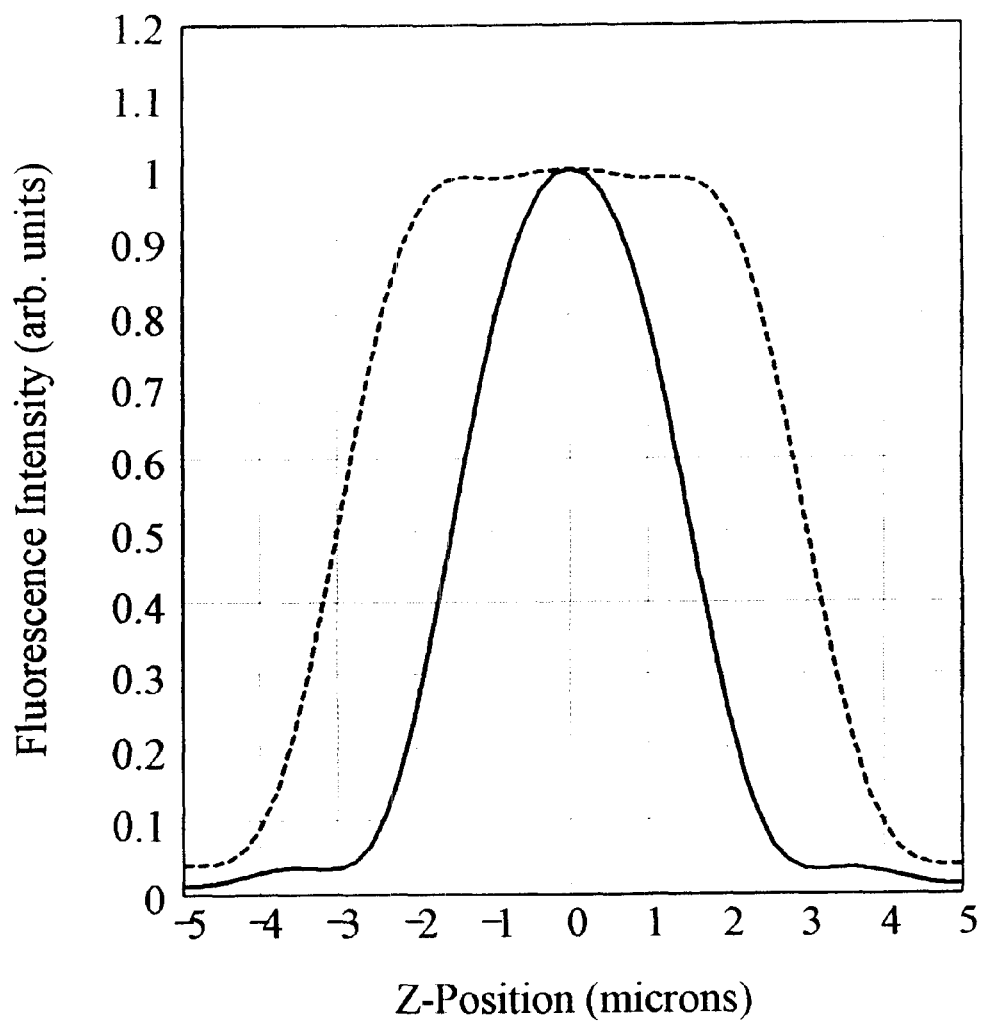
FIG. 9 shows similar plots as in FIG. 8, but for a numerical aperture of 0.8.

FIG. 9 shows similar plots as in FIG. 8, but for a numerical aperture of 0.8. Here, the observed FWHM's coincide well with the true height values.

Figure 10:
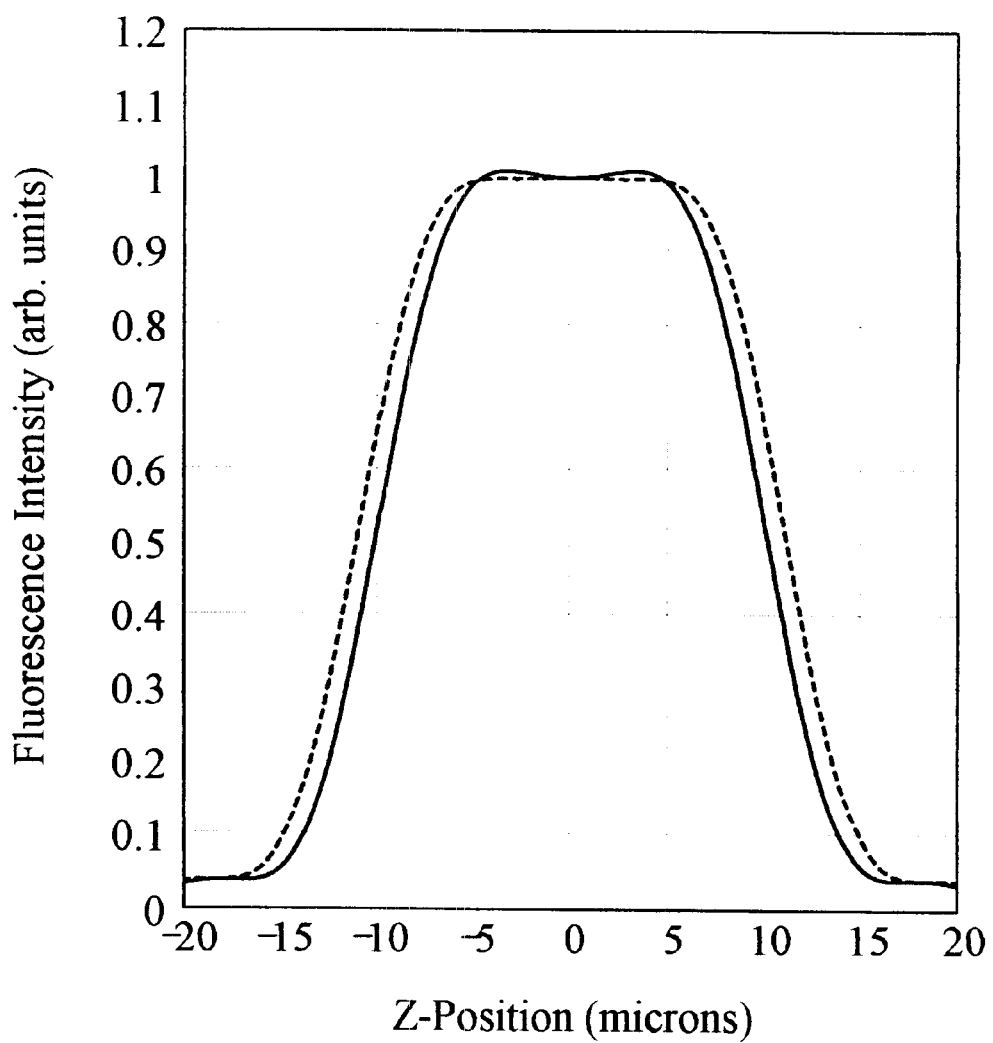
FIG. 10 shows similar plots as in FIG. 6, but assuming that the sample is not illuminated through the objective lens. The numerical aperture is 0.4.
Figure 11:
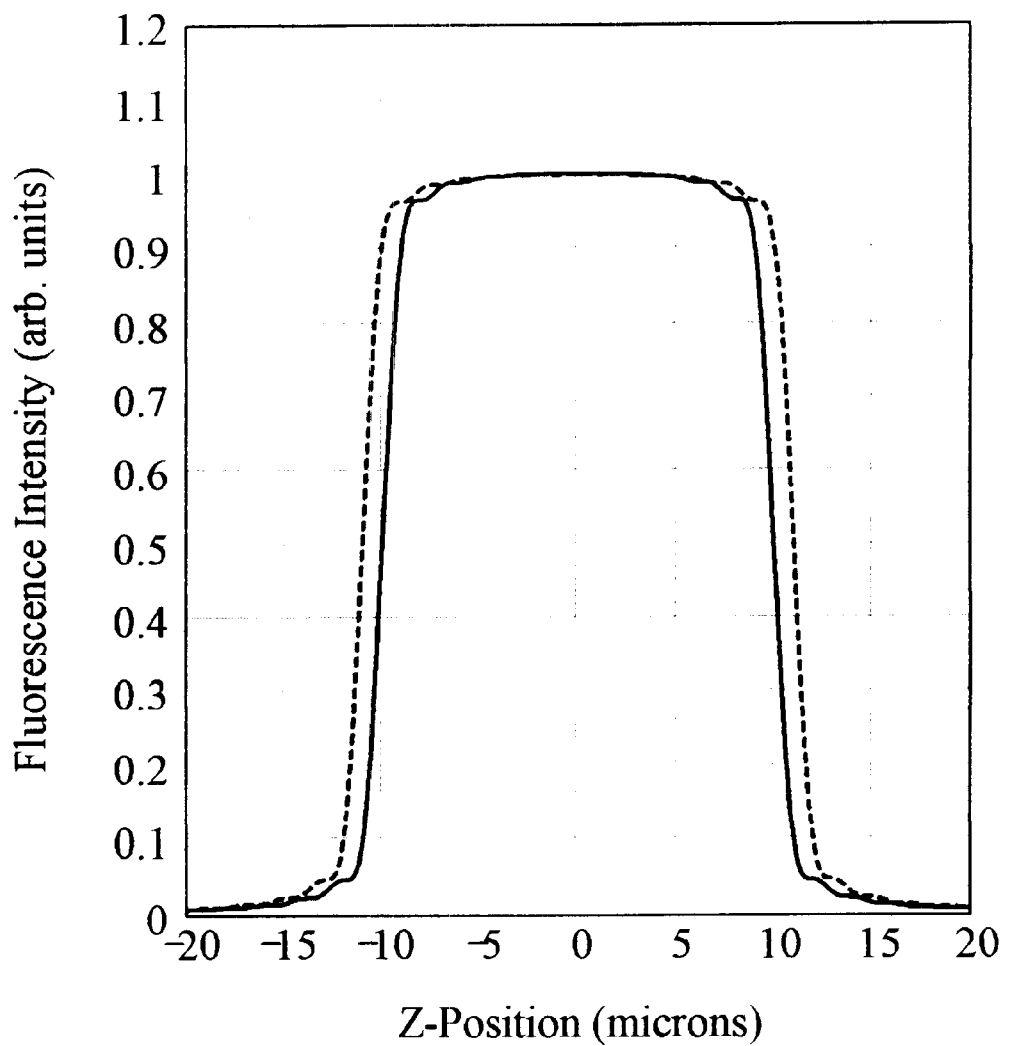
FIG. 11 shows similar plots as in FIG. 10, but for a numerical aperture of 0.8.

FIG. 10 shows similar plots as in FIG. 6, but assuming that the sample is not illuminated through the objective lens. The numerical aperture is 0.4. FIG. 11 shows similar plots as in FIG. 10, but for a numerical aperture of 0.8. In both cases, the observed FWHM's coincide well with the true height values, 20 and 22 microns.

So far, it has not been taken into account that, when the microscope's focal plane is shifted through the cuvette, the light is propagating at a different speed inside the cuvette due to the index of refraction, n, which is different from 1. The numerical aperture, NA=n*sinα is not changing inside the liquid sample, but the effective pathlength is longer than in air. Consequently, the observed FWHM has to be corrected to obtain the true cuvette height. According to the present invention, the true cuvette height is calculated from the observed FWHM value via the equation $$d = \frac{FWHM*n}{\sqrt{1-\left(\frac{NA}{n}\right)^2}}$$

where n is the index of refraction of the blood plasma.

It should be mentioned that the method of the present invention is not limited to the use of the FWHM-value. It would still be within the spirit of the invention to determine any other characteristic width of the fluorescence intensity vs. focal plane position curve, and to use that value for calculating the sample height. In this case, the relation between the used characteristic width and the FWHM has to be known.

I claim:

1. A method for calibrating the sample height of a sample in a chamber of a sample analyzer held within an imaging optical scanning instrument, said method comprising:
   a) providing said chamber for receiving a sample, in said sample analyzer;
   b) depositing a sample into said chamber wherein said sample contains a fluorescent dye;
   c) illuminating said sample with excitation light;
   d) scanning the sample with said instrument to detect the fluorescence from said sample;
   e) measuring fluorescence intensity values as a function of the focal plane position of the instrument relative to the sample;
   f) determining a characteristic width of the fluorescence intensity vs. focal plane position curve;
   g) calculating an approximate sample height from said characteristic width;
   h) calculating a corrected sample height value by taking into account the index of refraction of the sample; and
   i) obtaining the calibrated sample height.

2. The method of claim 1 wherein the characteristic width of the fluorescence intensity vs. focal plane position curve is the full-width-at-half-maximum, FWHM.

3. The method of claim 1 wherein the imaging optical scanning instrument is a fluorescence microscope.

4. The method of claim 1 wherein the imaging optical scanning instrument is a fluorescence microscope in EPI configuration.

5. The method of claim 1 wherein the imaging optical scanning instrument is equipped with a photodetector.

6. The method of claim 1 wherein the imaging optical scanning instrument is equipped with an imaging photodetector.

7. The method of claim 1 wherein said chamber is an optical cuvette.

8. The method of claim 1 wherein said sample is a liquid.

9. The method of claim 8 wherein the liquid sample contains particles in suspension.

10. The method of claim 9 wherein the measurement of fluorescence intensity values as a function of the focal plane position of the instrument relative to the sample is performed in particle-free locations within the sample.

11. The method of claim 10 wherein said fluorescent dye within the sample is selected so that it does not penetrate into the particles.

12. The method of claim 11 wherein said fluorescent dye is selected so that it absorbs excitation light and emits fluorescence light within spectral regions where the particles are only weakly absorbing.

13. The method of claim 8 wherein said sample is a biological fluid.

14. The method of claim 13 wherein said sample is blood.

15. The method of claim 8 wherein said sample is a suspension of cells.

16. The method of claim 2 wherein the sample height d is calculated from the FWHM-value FWHM using the equation $$d = \frac{FWHM * n}{\sqrt{1 - \left(\frac{NA}{n}\right)^2}}$$

where n is the index of refraction of the sample, and NA is the numerical aperture of the imaging optical scanning instrument.

* * * * *